(12) United States Patent
Lenormand et al.

(10) Patent No.: US 7,131,317 B2
(45) Date of Patent: Nov. 7, 2006

(54) METHOD AND DEVICE FOR EVALUATING PHYSICAL PARAMETERS OF AN UNDERGROUND DEPOSIT FROM ROCK CUTTINGS SAMPLED THEREIN

(75) Inventors: Roland Lenormand, Rueil Malmaison (FR); Patrick Egermann, Rueil Malmaison (FR); Daniel Longeron, Sartrouville (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 87 days.

(21) Appl. No.: 10/505,006

(22) PCT Filed: Feb. 19, 2003

(86) PCT No.: PCT/FR03/00547

§ 371 (c)(1),
(2), (4) Date: Aug. 19, 2004

(87) PCT Pub. No.: WO03/071253

PCT Pub. Date: Aug. 28, 2003

(65) Prior Publication Data

US 2005/0178189 A1 Aug. 18, 2005

(30) Foreign Application Priority Data

Feb. 21, 2002 (FR) .................................. 02 02242
Jan. 16, 2003 (FR) .................................. 03 00429

(51) Int. Cl.
*G01N 15/08* (2006.01)
(52) U.S. Cl. ........................................................ 73/38
(58) Field of Classification Search ................ 73/38
See application file for complete search history.

(56) References Cited

U.S. PATENT DOCUMENTS 3,140,599 A    7/1964  Rahme et al.
3,934,455 A *  1/1976  Harrisberger .................. 436/5
4,253,327 A    3/1981  Wiley
4,671,102 A *  6/1987  Vinegar et al. ............ 73/61.48
4,679,422 A *  7/1987  Rubin et al. ................... 73/38

(Continued)

FOREIGN PATENT DOCUMENTS

EP        1 167 948 A1    1/2002

(Continued)

*Primary Examiner*—Hezron Williams
*Assistant Examiner*—John Fitzgerald
(74) *Attorney, Agent, or Firm*—Antonelli, Terry, Stout and Kraus, LLP.

(57) ABSTRACT

A method and device evaluate simultaneously, with the same equipment, physical parameters such as the absolute permeability and the porosity of fragments taken from a fragmented natural or artificial porous medium. The porosity of the fragments is measured by means of helium pressure tests according to a protocol known in the art. The chamber (1) containing the fragments is communicated with a tank (11) whose volume is also known and containing helium at a known pressure. At pressure balance, the value of the solid volume can be deduced. The rock envelope volume and the fragments mass are also measured. Combining these measurements allows to determine the porosity of the samples and the density of the rock. Their permeability is then measured by immersing them in a viscous fluid and by communicating the chamber with viscous fluid at a determined pressure contained in a vessel (9) so as to compress the gas trapped in the pores of the rock, according to two different protocols. The values of the physical parameters are determined by modelling the evolution of the pressure or of the volume in the chamber and by means of an iterative adjustment.

16 Claims, 8 Drawing Sheets

U.S. PATENT DOCUMENTS

| | | | |
|---|---|---|---|
| 5,050,493 A * | 9/1991 | Prizio et al. ................. 100/106 |
| 5,193,059 A | 3/1993 | Tiab et al. |
| 5,245,859 A | 9/1993 | Smith et al. |
| 5,261,267 A | 11/1993 | Kamath et al. |
| 5,373,727 A | 12/1994 | Heller et al. |
| 5,394,737 A * | 3/1995 | Prange et al. ................... 73/38 |
| 5,513,515 A * | 5/1996 | Mayer ........................... 73/38 |
| 5,637,796 A * | 6/1997 | Deruyter et al. ......... 73/152.09 |
| 5,679,885 A * | 10/1997 | Lenormand et al. ........... 73/38 |
| 5,832,409 A | 11/1998 | Ramakrishnan et al. |
| 5,844,136 A * | 12/1998 | Marsala et al. ................ 73/38 |
| 6,021,662 A * | 2/2000 | Moulu et al. ................... 73/38 |
| 6,453,727 B1 * | 9/2002 | Lenormand et al. ........... 73/38 |
| 6,871,532 B1 * | 3/2005 | Zazovsky ................ 73/152.05 |

FOREIGN PATENT DOCUMENTS

EP      1 170 582 A1      1/2002

* cited by examiner

METHOD AND DEVICE FOR EVALUATING PHYSICAL PARAMETERS OF AN UNDERGROUND DEPOSIT FROM ROCK CUTTINGS SAMPLED THEREIN

FIELD OF THE INVENTION

The present invention relates to a method and to experimental devices for evaluating, with the same equipment and simultaneously, the porosity and the absolute permeability of any fragmented natural or artificial porous medium and notably of a zone of an underground reservoir containing hydrocarbons or other fluids, from rock samples taken from this medium. The samples can be, for example, fragments obtained during well drilling operations: drilling cuttings or fragments obtained by crushing bigger samples: cores or lateral cores taken in a well.

The current petroleum context leads operators to take an interest in new zones (deep offshore) and in new reservoir types (marginal structures located close to existing surface installations). Considering the drilling costs linked with the difficult environment of these new discoveries or with the limited size of certain structures, operators can no longer afford to drill complementary appraisal wells without risking compromising the economic viability of the project. The development strategy set before starting production is therefore less strict so as to allow <<real-time>> adaptation to the nature of the information collected by drilling production wells. This is referred to as appraisal development.

Petrophysical measurements have a key role in the assessment of the quality of a reservoir. However, the time required for this type of measurements is often very long and therefore incompatible with the reactivity necessary for the success of appraisal developments. New, faster and less expensive evaluation means are thus required as a support to decision-making.

Cuttings carried along by the drilling mud have been subjected to examinations in the field for a longtime. They are carried out by the crews in charge of mud logging and they essentially help to complete the description of the geologic layers drilled, performed from logs.

BACKGROUND OF THE INVENTION

Work has already been done to try to evaluate petrophysical properties from cuttings. The acoustic properties as regards S and P waves (shear and compressional waves) have been measured for example. Various parameters have also been studied, such as the hardness and the deformation of the rock fragments, or their porosity and permeability.

According to a first known method intended for permeability measurement, the rock fragment is first coated with resin. A thin slice is cut out of the coated rock and placed in a measuring cell. It comprises means for injecting a fluid under pressure at a controlled flow rate and means for measuring the pressure drop created by the sample. Since the resin is impermeable, the absolute permeability is deduced from Darcy's equation by taking account of the real surface area occupied by the rock fragments.

This method is for example described by:

Santarelli F. J., et al.; <<Formation evaluation from logging on cuttings >>, SPERE, June 1998, or Marsala A. F., et al.; <<Transient Method Implemented under Unsteady State Conditions for Low and Very Low Permeability Measurements on Cuttings >>, SPE/ISRM No.47202, Trondheim, 8–10 Jul. 1998.

This type of measurement can only be obtained in the laboratory after long fragment conditioning operations.

Another well-known method is based on an NMR (Nuclear Magnetic Resonance) measurement which is directly carried out on the cuttings after prior washing followed by brine saturation. This type of measurement gives a porosity value that can be directly used. The permeability K is determined by means of correlations of the same nature as those used within the context of the NMR logging.

An illustration of this method can be found in the following document:

Nigh E., et al. ; P-K™ : Wellsite Determination of Porosity and Permeability Using Drilling Cuttings, CWLS Journal, Vol.13, No.1, Dec. 1984.

European patent application EP-1,167,948 describes a system for evaluating physical parameters such as the absolute permeability of porous rocks from a zone of an underground reservoir, from rock fragments taken in this zone, such as rock fragments carried along by the drilling mud. After immersing the fragments in a viscous fluid contained in a chamber, a fluid whose pressure increases with time, up to a predetermined pressure threshold, is injected so as to compress the gas trapped in the pores of the rock. This injection stage is followed by a relaxation stage where injection is stopped. The pressure variation during these two successive stages is recorded. The evolution of the pressure during the injection process having been modelled from initial values selected for the physical parameters of the fragments, the computer adjusts them iteratively so as to obtain the best possible match between the modelled pressure curve and the pressure curve really measured.

SUMMARY OF THE INVENTION

The object of the method according to the invention is to evaluate, with the same equipment and simultaneously, physical parameters such as the absolute permeability and the porosity of a fragmented natural or artificial porous medium such as a zone of an underground reservoir, from rock fragments taken in this medium. It comprises a stage of immersing the fragments contained in a containment chamber in a viscous fluid and of communicating the chamber containing the fragments with a source of fluid. under pressure so as to compress the gas trapped in the pores of the rock, a stage of measuring a physical quantity indicative of the evolution of the fluid absorption by the rock, modelling the evolution of the physical quantity in the chamber, from initial values for the physical parameters of the fragments, and a stage of iterative adjustment of the values of the physical parameters of the rock fragments so as to obtain the best possible adjustment of the modelled evolution with the measured evolution of the physical parameter in the chamber.

The method is characterized in that:

during the stage of immersion, in the viscous fluid, of the fragments contained in containment chamber (1), the injection pressure of the fluid or of the volume of fluid injected is measured, during the modelling stage, the evolution of the injection pressure of the fluid or of the volume of fluid injected is modelled from initial values selected a priori for permeability (K) and the residual gas saturation and porosity ($\Phi$), and during the adjustment stage, the value of the permeability and of the porosity of the rock fragments is iteratively adjusted so as to obtain the best possible adjustment between the modelled pressure or injected volume evolution and the measured evolution of the pressure or of the volume injected in the chamber.

According to an embodiment, the method comprises a prior stage of feeding the washed and dried rock fragments into the containment chamber which is first communicated with a gas tank at a predetermined pressure, so as to determine the solid volume of the fragments, the envelope volume and the mass of the fragments are measured, and the porosity and the density of the rock fragments are deduced therefrom. In the modelling stage, the evolution of the injection pressure of the fluid or of the volume of fluid injected is modelled from initial values selected a priori for permeability (K) and the residual gas saturation, and from the value measured for porosity ($\Phi$), and in the adjustment stage, only the value of the rock fragments permeability is iteratively adjusted so as to obtain the best possible adjustment between the modelled evolution of the pressure or of the volume injected and the measured evolution of the pressure or of the volume injected in the chamber.

According to an embodiment, the stage of communicating the vessel containing a fluid at a predetermined pressure with a viscous fluid comprises a short communication time so as to cause a fast pressure increase in the chamber and compression of the gas trapped in the pores of the rock, followed by a relaxation period after isolation of the chamber, and the evolution of the pressure in the chamber during the two periods is measured.

According to an embodiment, the stage of communicating the chamber with a viscous fluid comprises communicating the chamber with the vessel containing fluid at a predetermined pressure so as to cause a fast and prolonged pressure increase in the chamber and compression of the gas trapped in the pores of the rock, and the evolution of the volume of fluid injected as a function of time is measured (N.B. Procedure III).

In applications where the medium is an underground reservoir, the containment chamber can be filled with drilling cuttings or rock fragments obtained by crushing cores taken in a well, notably cores obtained by sidewall coring of a well, whether invaded by drilling fluids or previously cleaned.

The device for implementing the method mainly comprises a containment chamber for the fragments, means for injecting first a viscous fluid into the chamber so as to fill the chamber containing fragments of the medium, and for carrying out a cycle comprising a stage of fluid injection into the chamber, means for measuring the evolution of a physical quantity in the chamber and a processing system for modelling the evolution of this quantity from initial values selected for the physical parameters of the rock fragments, and for adjusting iteratively the values to be given to these physical parameters so as to obtain the best possible adjustment between the modelled evolution of the physical quantity and the measured evolution of said quantity in the chamber. It further comprises a vessel containing a fluid at a determined pressure (such as a surge bottle containing viscous oil and a gas cap at a predetermined pressure), and means controlled by the processing system and intended to control communication of the vessel with the chamber containing the rock fragments.

In cases where the device is also used to determine the porosity of the fragments, it further comprises a gas tank that can be communicated with the chamber by means of a valve, an instrument for measuring the volume envelope so as to determine the porosity of the fragments and means for measuring the mass of the fragments.

The device comprises, for example, means for measuring the evolution of the pressure in the chamber, as a function of time, the processing system being suited for modelling the evolution of the pressure (or of the volume) of the viscous fluid injected in the chamber, from initial values selected for the physical parameters of the rock fragments, and for iteratively adjusting the values to be given to these physical parameters so as to obtain the best possible adjustment between the modelled pressure evolution and the measured evolution of the pressure (or of the volume) in the chamber.

The means for measuring the evolution of the volume of fluid injected include, for example, a flowmeter or differential pressure detector, and the means for measuring the envelope volume of the fragments to be tested is for example a powder pycnometer.

The method proves to be satisfactory for very varied rocks within a wide permeability and porosity range.

Considering the limited space occupied by the device, its ease of use and the rapidity with which the measurements and the adjustment between the theoretical data and the experimental data can be performed, the method is particularly well-suited for field conditions. It is therefore possible to carry out measurements and interpretations directly in the field in a very short time, which has nothing in common with the time required to obtain equivalent results by means of laboratory methods. This opens up interesting prospects for petrophysical characterization in the petroleum and hydrologic sphere, permeability, porosity, rock density, since it is possible to take advantage of this new source of information as a support for the interpretation of electric logs and to fine down the evaluation of a well in terms of production potential. This also opens up important prospects for the petrophysical characterization of any other fragmented natural or artificial porous medium.

BRIEF DESCRIPTION OF THE DRAWINGS

Other features and advantages of the method and of the device according to the invention will be clear from reading the description hereafter of embodiments given by way of non limitative example, with reference to the accompanying drawings wherein.

DETAILED DESCRIPTION

Figure 1:
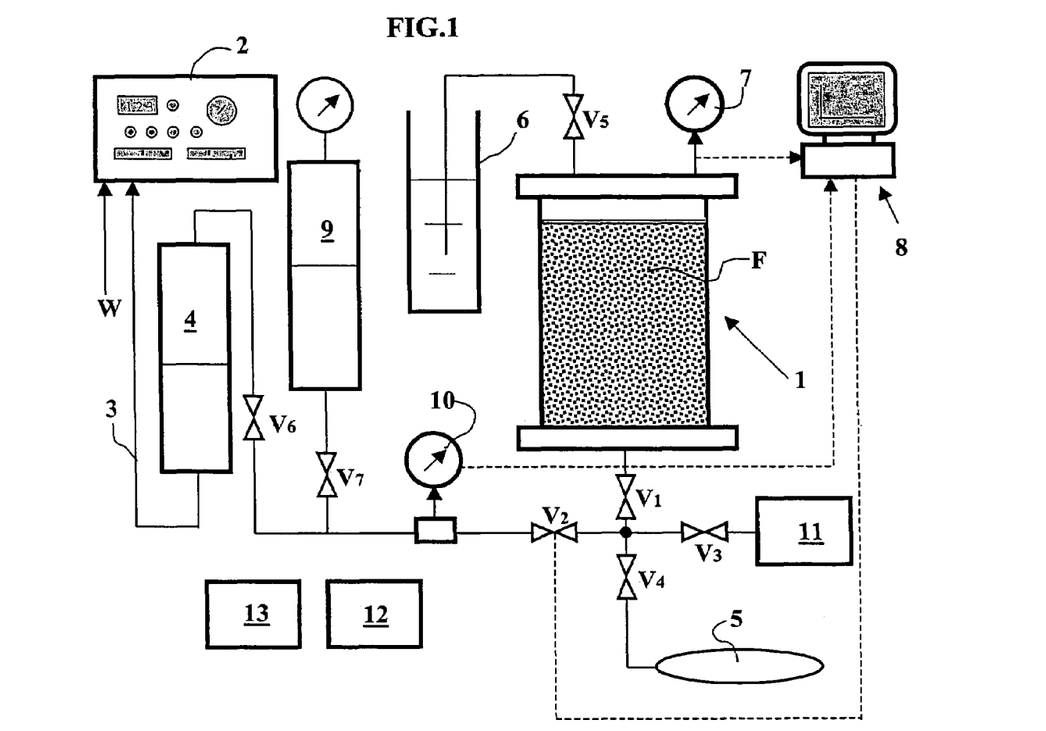
FIG. 1 diagrammatically shows the device.

The device diagrammatically shown in FIG. 1 comprises a containment chamber 1 in which the drilling cuttings are initially placed. A constant-feed water pump 2 communicates through a line 3 with the base of a surge tank 4 containing a high-viscosity oil. The opposite end of surge tank 4 communicates through a valve V6 with a line L1. A first end of containment chamber 1 communicates with line L1 through the agency of two valves V1, V2. The opposite end of containment chamber 1 communicates, by means of an isolating valve V5, with a separator 6. A manometer 7 is connected to the outlet of chamber 1. The pressure variations measured by manometer 7 are acquired by a processor 8 such as a microcomputer. Valve V2 is directly controlled by processor 8. Line L1 also communicates by means of a valve V7 with a surge tank 9 containing viscous oil placed under a predetermined pressure by a gas cap under pressure. A flowmeter or a differential pressure detector 10 can be placed, if necessary, on line L1 between chamber 1 and tank 9 to measure the flow rate of the fluid injected.

Fragments available after cleaning, from which all the fluids have been previously removed, can also be used. In cases where containment chamber 1 is filled with cleaned fragments, helium coming from a bottle 5 is injected by opening a valve V4 so as to expel the air from the chamber.

Chamber 1 is also connected, by means of valves V1 and V3, to a tank 11 filled with helium and whose volume is known. Chamber 1 can be communicated with tank 11 initially at a known pressure by opening V1 or V3, valves V2 and V4 being closed.

The device further comprises a balance 12 and a powder pycnometer type instrument 13 allowing to measure the envelope volume of the fragments introduced.

I) Porosity Measurement

Determination of the porosity comprises a stage of acquisition of experimental measurements of the envelope volume Ve of the fragments introduced, of the solid volume Vs of rock introduced and of the mass $m_e$ of rock introduced, and a stage of calculation of the porosity and of the density of the rock.

a) Measurement Acquisition

The cleaned and dried fragments are previously weighed on balance 12 and their envelope volume is measured by means of instrument 13. The fragments are then fed into containment chamber 1 placed under helium atmosphere through communication with helium tank 5 so as to expel the air. Chamber 1 is then connected to tank 11 filled with helium, whose volume is known, by opening valves V1 and V3, valves V2 and V4 being closed. The balance pressure allows to deduce the value of the solid volume of the rock from the initial pressures in chamber 1 and tank 11 and from their volumes. All these measurements allow to determine the porosity of the samples. The density of the rock is also obtained by measuring the mass of the fragments introduced.

Envelope volume Ve is obtained by means of a powder pycnometer according to a technique known to specialists.

Let P1 be the initial pressure in 1, Ph the initial pressure in tank 11, Pe the balance pressure after communication, U1 the volume of chamber 1, Vh the volume of tank 11 and mc the mass of the fragments used.

Vs, φ and d are respectively the solid volume, the porosity and the density of the rock. We have:

$$Vs = U1 - Vh\frac{(Ph - Pe)}{(Pe - P1)}$$

$$\phi = \frac{Ve - Vs}{Ve}$$

$$d \text{ rock} = \frac{mc}{Ve}.$$

Figure 11:
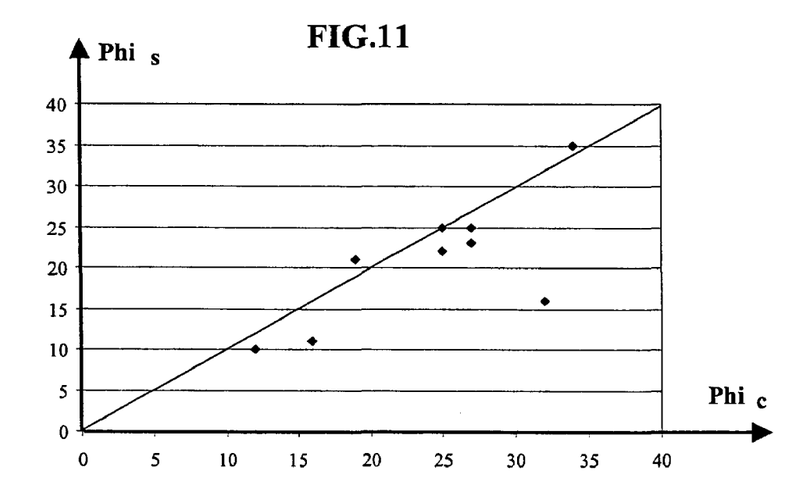
FIG. 11 shows the good match obtained between the values of the porosity (Φ or $Phi_c$) of the rock fragments tested and those ($Phi_s$) obtained for samples or cores in cases where the a-priori values of the porosity and of the permeability are iteratively adjusted.

FIG. 11 shows that a very good estimation of the porosity of the rocks tested is obtained.

II) Permeability Estimation

Estimation of the absolute permeability essentially comprises three stages:

1) a stage of acquisition of experimental measurements of the pressure variations (procedures 1 and 2) or of the evolution of the volume injected (procedure 3) from the drilling fragments, which leads to experimental curves, 2) a stage of modelling the physical phenomena occurring in the drilling fragments during the same operating cycle, for arbitrary values of the physical parameters sought (permeability K and porosity φ involved in the model, allowing to establish similar theoretical curves, and 3) an adjustment stage wherein the values to be given to the physical parameters involved in the model are determined so as to obtain the best possible adjustment between the experimental curves and the theoretical curves.

1) Measurement Acquisition

Chamber 1 is filled with a high-viscosity oil by means of the pump. The oil occupies the free space between the drilling fragments and it also flows, by spontaneous imbibition, into the rock. A degassing whose intensity and duration depend on the nature of the rock (mainly the porosity) takes place. This degassing only involves part of the gas. A certain residual volume remains trapped in the drilling fragments in form of disconnected pockets.

There are three possible procedures for the experimental stage:

Procedure 1

As already described in detail in the aforementioned European patent application, procedure 1 essentially consists in injecting, at a constant flow rate, oil coming from surge tank 4 by gradually raising the injection pressure by means of pump 2 (part C1 of the pressure curve). The amount of oil entering the pores of the rock as the residual gas trapped in the pores is compressed is measured. When the pressure reaches a predetermined threshold $P_M$, oil injection is stopped. A relaxation then takes place. The fluids tend to rebalance in the drilling fragments and a slow return to balance of the pressure is observed (part C2 of the pressure curve, FIG. 3).

Procedure 2

The second procedure essentially consists in communicating chamber 1, which contains rock fragments C, with surge tank 9 which contains viscous oil under pressure by opening valve V2 controlled by computer 8.

Figure 6:
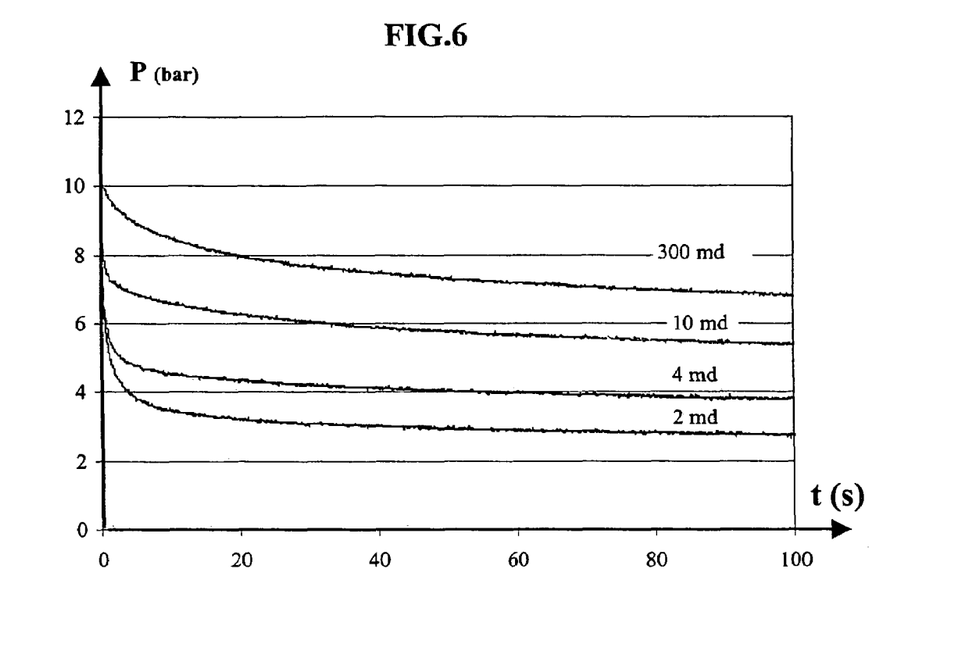
FIG. 6 shows experimental pressure evolutions within the context of a second procedure.

Initially, the valve is closed. On the side of surge tank 9, the pressure is Pmax, whereas on the side of chamber 1, the pressure is equal to the ambient pressure. Valve V2 controlled by computer 8 is then opened for some tenths of a second so as to rapidly increase the pressure in chamber 1 up to pressure Pmax, then this valve is closed again and a pressure relaxation is observed, which also corresponds in this case to a return to balance of the pressure in the rock fragments (FIG. 6). In relation to procedure 1, the pressure rise time is minimised, which increases the sensitivity of the system in terms of permeability detection. On the other hand, this procedure is less precise in terms of volumetric balance (oil injected) in relation to the constant-feed injection.

Procedure 3

In relation to the previous two procedures which include an injection period and a relaxation period, this procedure comprises a single stage (injection). The experiment is prepared exactly under the same conditions as for procedure 2. The flowmeter or differential pressure detector 10 is added on the line connecting chamber 1 to surge tank 9 (FIG. 1). Initially, the conditions are the same as in procedures (the flowmeter or the differential pressure detector are initially under pressure). Valve V2 is then simply opened and the evolution of the flow rate or of the differential pressure with time is recorded. When using the differential detector, a calibration curve previously measured by means of pump 2, which gives the relation between the flow rate of the viscous oil and the differential pressure, is used. This also allows to convert the experimental differential pressure measurements and to deduce the evolution of the volume of oil injected with time. The evolution of the volume injected is directly obtained if a flowmeter is used.

In relation to the previous procedures, this approach allows to simplify the course of the experiment while keeping good control of the volume injected, which facilitates acquisition of the measurements and interpretation of the results with the simulator. Besides, since the <<parasitic>> part of the gas trapped outside the fragments or cuttings C (inter-fragment space and system compressibility) is compressed during the first moments of the experiment, a sort of natural decorrelation of the signal is observed, which allows to explore, for the same size, much wider permeability ranges in relation to the other methods, and also to better measure the volume of gas actually trapped in the cuttings.

FIGS. 3A to 3D show examples of the evolution of the pressure signal observed for fragments of four different rocks, for a flow rate of 480 cc/h (procedure 1). Whatever the rock considered, the same general pressure evolution is observed. A progressive rise is observed during the injection stage as the residual gas is compressed. The time required to increase the pressure by 5 bars ranges from 15 to 40 seconds, according to the rocks and to the initial volume of gas trapped. As soon as injection is stopped, the pressure decreases. Although this decrease is significant for rocks 1 and 2, it remains more moderate for rocks 3 and 4. A gradual stabilization of the signal is observed in the long term.

FIG. 6 shows examples of evolution of the pressure within the context of procedure 2. As in the context of procedure 1, significant variations of the relaxation curves are observed according to the nature of the rocks tested. The lower the permeability of the rocks, the more marked the relaxation pressure.

Figure 8:
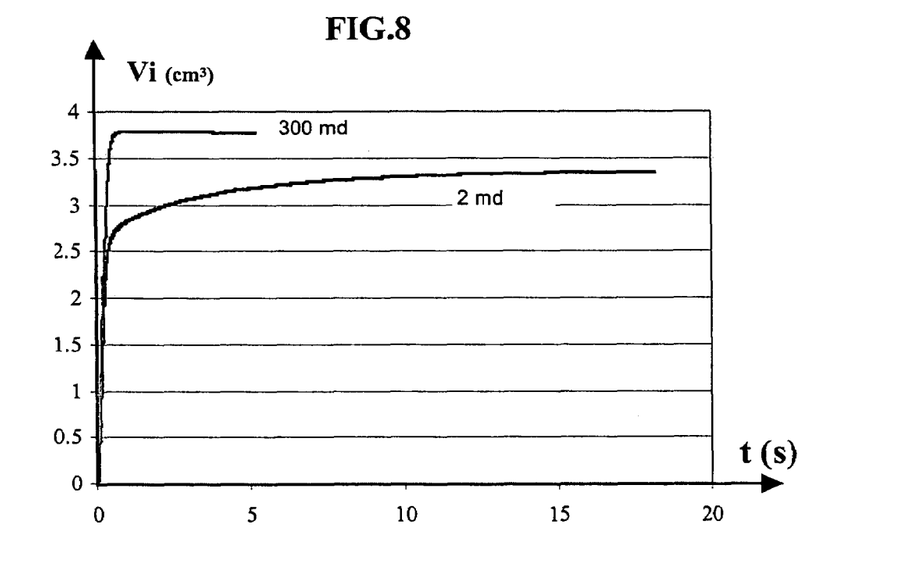
FIG. 8 shows experimental evolutions of a volume of oil injected into the chamber containing the fragments, within the context of a third procedure.

FIG. 8 shows examples of evolution of the pressure within the context of procedure 3. Significant variations of the filling curves are observed according to the nature of the rocks tested. The lower the permeability of the rocks, the slower the filling kinetics. The higher the porosity of the rocks, the greater the cumulative volume of oil injected.

The goal of the next two stages is to obtain, from the pressure or injected oil volume measurements, an estimation of permeability K alone (if the porosity has been measured before as described above) or a combined estimation of permeability K and of porosity ($\phi$).

2) Modelling

The drilling cuttings are considered to be of homogeneous size and of spherical shape, and the gas is assumed to be perfect. The pressure drop due to the viscosity of the gas is disregarded in relation to that of the oil, considering the difference between the viscosities. The residual gas trapped in the rock fragments after spontaneous imbibition of the oil has the form of disconnected homogeneously distributed pockets. The capillary pressure is also considered to be negligible.

Figure 2:
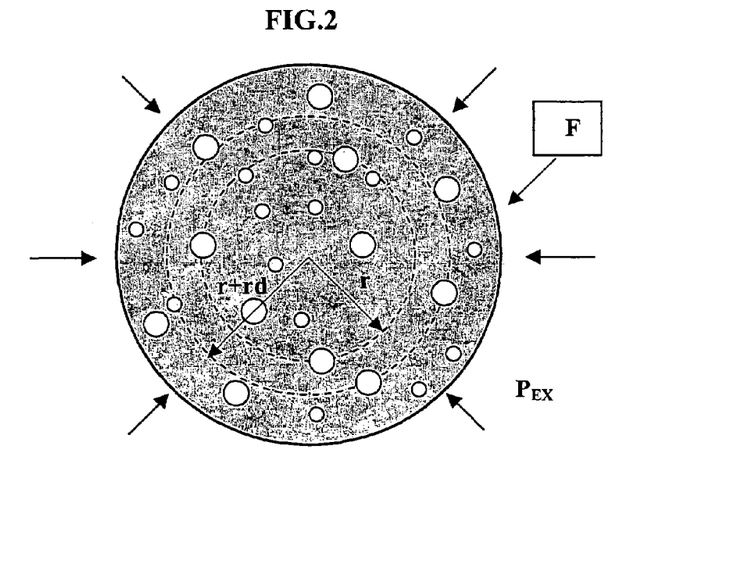
FIG. 2 diagrammatically shows the structure of a fragment or particle of a porous rock wherein the effects of the injection of a high-viscosity fluid such as oil are modelled, FIGS. 3A to 3D diagrammatically show the variation curves of the pressure prevailing in the chamber of the device of FIG. 1, during the injection and relaxation stages, for four different rocks with experimental procedure 1.
Figure 3A:
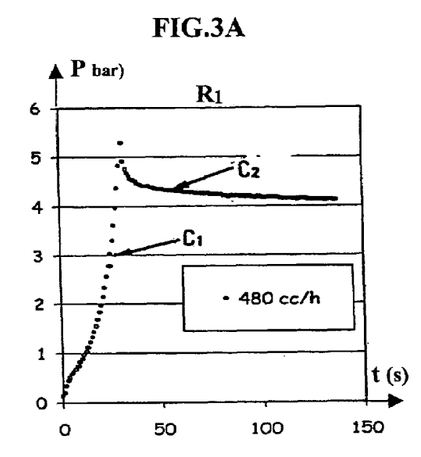
Figure 3B:
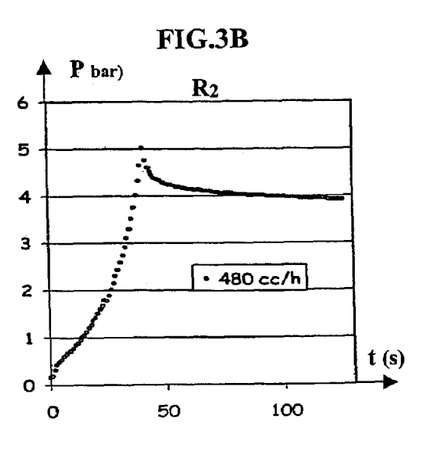
Figure 3C:
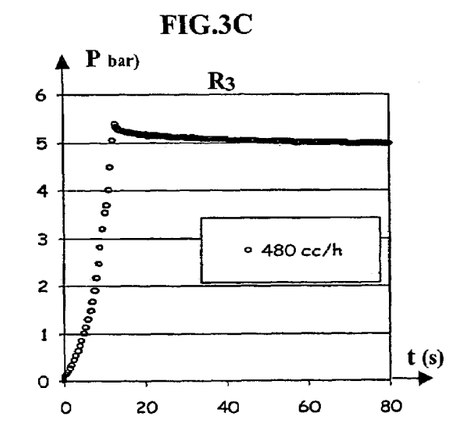
Figure 3D:
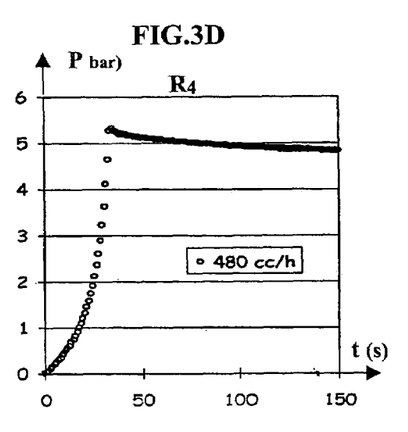

Considering the spherical shape of the fragments, we will consider a cap of thickness dr (FIG. 2) and calculate the evolution of the pressure at the boundary of the rock particle when a flow of oil q is injected.

We consider that the total flow rate Q of the fluid injected is equitably divided among the N rock particles and that each one receives the flow rate $$q = \frac{Q}{N}.$$

The perfect gas law allows to deduce the local gas saturation $S_g$ from the moment that the pressure $$P: S_g = S_{g0}\frac{P_0}{P}$$

($P_0$ is the pressure of the oil) is known. In the cap, a material balance is performed on the oil. The accumulation is equal to the difference between what goes in and what goes out. We deduce therefrom that:

$$div\vec{V}_0 + \phi\frac{\partial S_0}{\partial t} = 0.$$

Since $$S_0 = (1 - S_g) = \left(1 - S_{g0}\frac{P_0}{P}\right),$$

we deduce that:

$$\frac{\partial S_0}{\partial t} = \frac{\partial S_0}{\partial P}\frac{\partial P}{\partial t} = \left(S_{g0}\frac{P_0}{P^2}\right)\frac{\partial P}{\partial t}$$

Besides, since $$\vec{V}_0 = -\frac{K}{\mu_0}\vec{grad}P_0$$

(K is the permeability and $\mu_0$ the viscosity of the oil), and since the capillary pressure can be considered to be negligible, so that we have $P_0=P_{gas}=P$, the previous equation can be written in the following form:

$$-\frac{K}{\mu_0}\Delta P + \phi S_{g0}\frac{P_0}{P^2}\frac{\partial P}{\partial t} = 0.$$

It follows therefrom that:

$$\Delta P = \frac{\mu_0 \phi S_{g0}}{K}\frac{P_0}{P^2}\frac{\partial P}{\partial t}.$$

We therefore obtain the conventional form of a diffusion type equation with, however, a $1/P^2$ term factor of the accumulation due to the compressible nature of the gas.

In spherical coordinates, the Laplacian is $$\frac{1}{r^2}\frac{\partial}{\partial r}\left(r^2\frac{\partial P}{\partial r}\right).$$

Finally, the equation to be solved is written as follows:

$$\frac{\partial}{\partial r}\left(r^2\frac{\partial P}{\partial r}\right) = \alpha\frac{r^2}{P^2}\frac{\partial P}{\partial t} \text{ with} \quad (1)$$

$$\alpha = \frac{\mu_0 \phi S_{g0} P_0}{K}. \quad (2)$$

As it is injected, the oil expels the air in the free space between the drilling fragments and it enters the rock by spontaneous imbibition. Despite certain precautions, a certain volume of gas may remain outside because of the non-regular shape of the drilling cuttings. This trapped volume ($V_{gp}$) plays a direct part in the general form of the pressure response and it has to be taken into account in the solution.

A certain compressibility due to the experimental device also has to be taken into account. It comes from the chamber, from the lines as well as from the properties of the oil. The equivalent compressibility observed is of the order of 0.0005 bar$^{-1}$.

As the oil used is saturated with gas at atmospheric pressure, dissolution phenomena occur when the pressure rises during measurement. These aspects are taken into account by introducing a diffusion parameter representative of the molecule exchanges at the level of the gas/oil interfaces.

The diffusion equation is solved by means of the finite-difference method with an explicit scheme and by applying the boundary conditions in time $P(r,0)=P_{atm}$ and in space $P(R,t)=P_{ext}$, and $$\frac{\partial P}{\partial r}(0,t) = 0.$$

When imposed-pressure experiments are simulated, pressure Pext is known and the equation is solved in an explicit way. When imposed flow rate experiments are simulated, the value of Pext is calculated by means of a convergence loop whose test is based on a comparison between the saturation of gas remaining in the rock particle and the value obtained by volume balance from the amount of oil injected.

The solution of the diffusion equation during the relaxation period (procedures I and II) is identical and it is based on the same convergence loop. Only the test condition changes since, as injection is stopped, the volume of gas is maintained in the rock particle.

3) Adjustment of the Model to the Experimental Results

The model is implemented in a calculator such as computer 8 (see FIG. 1) in form of a software and it is inserted in an iterative optimization loop. The model is operated with permeability K and residual gas saturation values selected a priori, by imposing for porosity ($\Phi$) the value obtained experimentally, and the resulting simulated pressure curve is compared with the experimental curve, by successive iterations, by changing the values of K and of the residual gas saturation in the model. The values that allow the best possible adjustment of the theoretical and experimental curves according to a conventional Newtonian or gradient type optimization method are thus found.

In cases where porosity ($\Phi$) has not been previously measured experimentally, the model is operated with permeability K, residual gas saturation and porosity values selected a priori, and the resulting simulated pressure curve is compared with the experimental curve, by successive iterations, by changing the values of K and $\Phi$ and the residual gas saturation values in the model. FIG. 11 shows that a satisfactory estimation of the porosity of the rocks tested is obtained.

Figure 12:
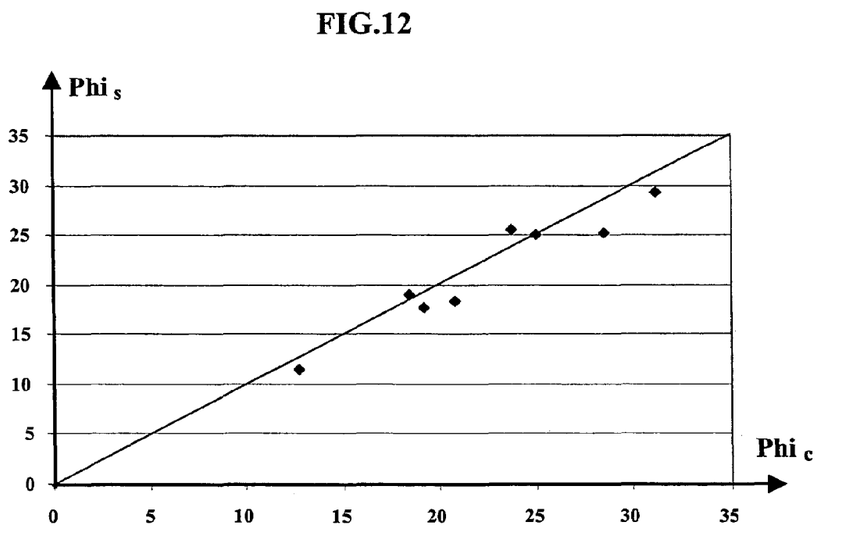
FIG. 12 shows the improved result of the porosity determination of the rock fragments tested when the porosity ($Phi_c$) of the fragments is first measured experimentally.

When the value of the previously measured porosity is known, only the permeability value K has to be adjusted in the modelling stage. The modelling operation is therefore faster. It is also more accurate, as can be clearly seen in FIG. 12.

FIGS. 5A to 5D show the good match that is rapidly obtained, by successive iterations, between the theoretical and experimental curves for four rock fragments tested by means of procedure 1. As can also be seen in FIG. 4, the results obtained by applying the method are quite comparable to those obtained in the laboratory after long conditioning periods using conventional methods for several rocks of different permeabilities.

Figure 7A:
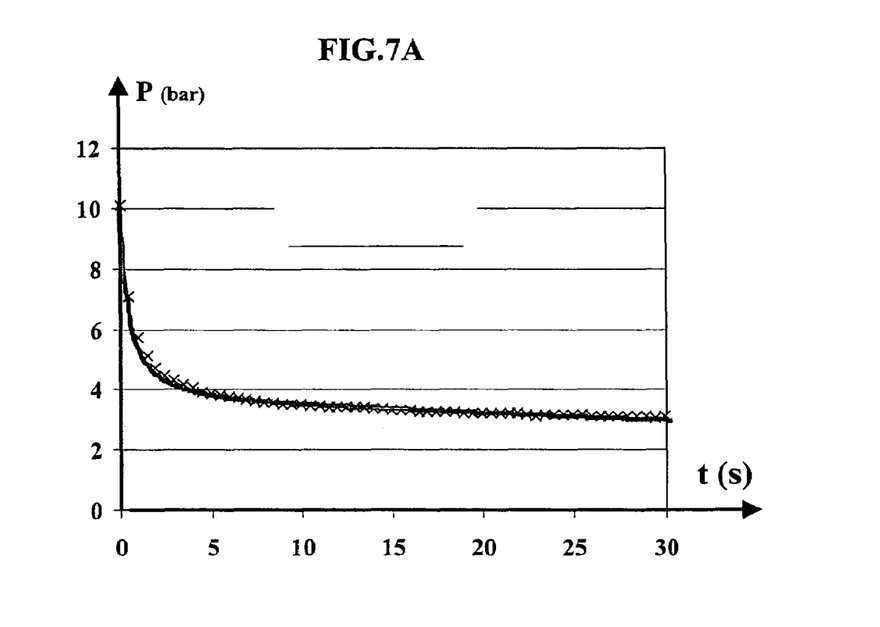
FIGS. 7A and 7B show two examples of adjustment (full line) to the experimental curves (in form of crosses) within the context of the second procedure.
Figure 7B:
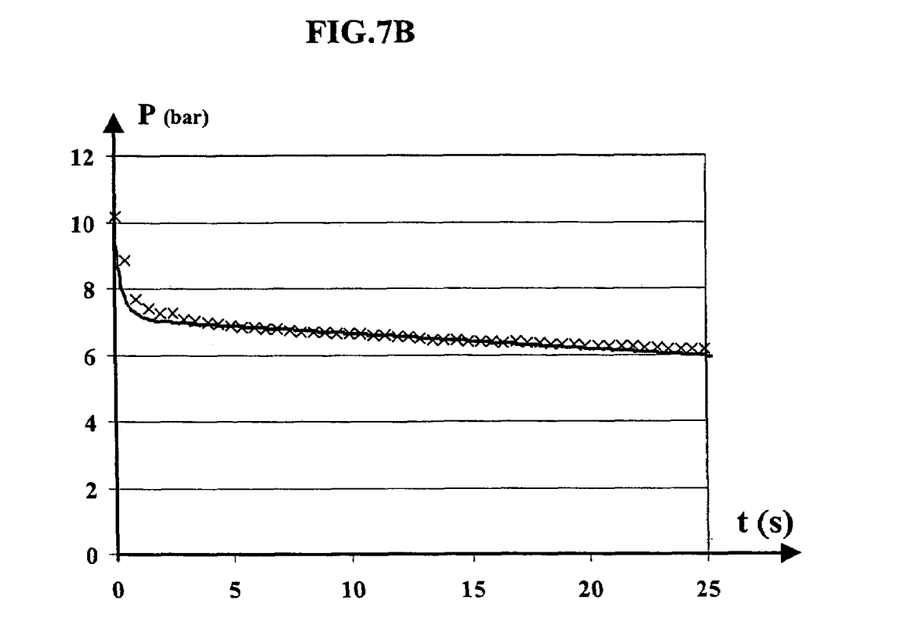

FIGS. 7A and 7B show two examples of adjustment by successive iterations on experimental results using procedure 2.

Figure 9A:
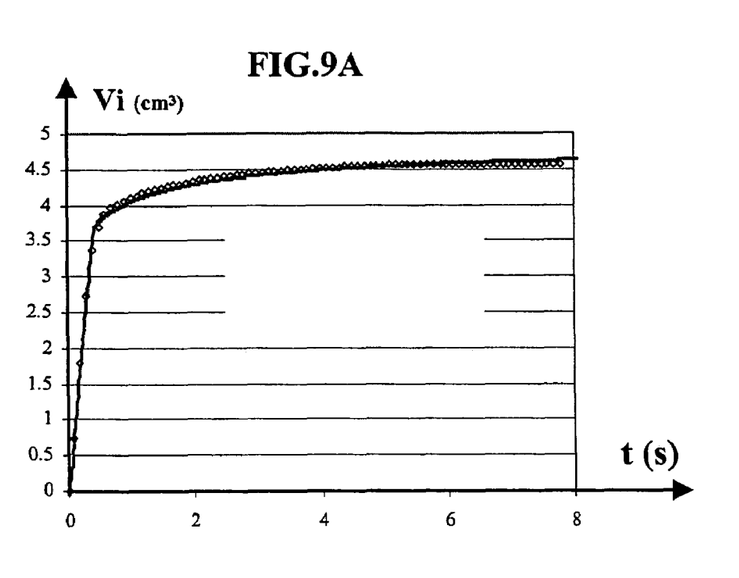
FIGS. 9A and 9B show two examples of adjustment (in form of diamonds) to the experimental curves (full line) within the context of the third procedure.
Figure 9B:
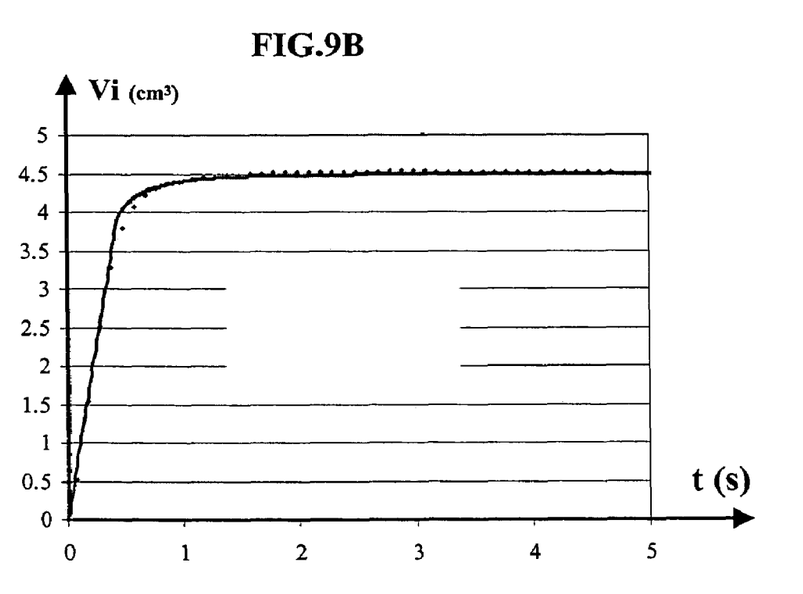

FIGS. 9A and 9B show two examples of adjustment by successive iterations on experimental results using procedure 3.

Figure 4:
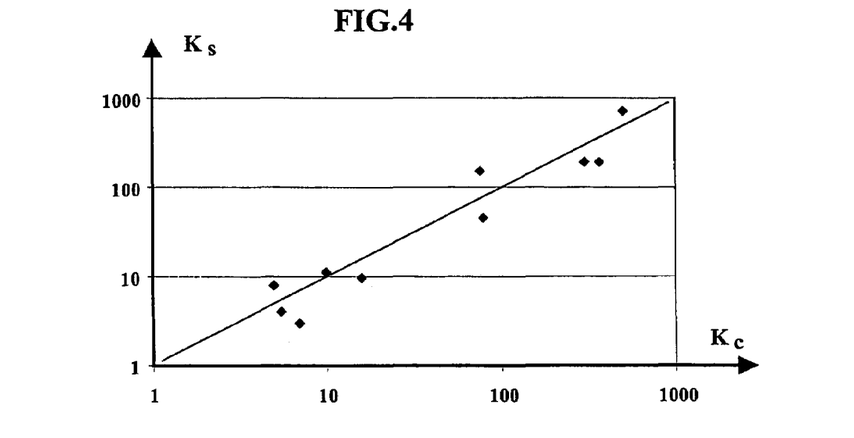
FIG. 4 shows the good match between the permeabilities obtained for several rock types by means of a conventional core measuring method and by means of the method according to the invention (procedure 1)
Figure 5A:
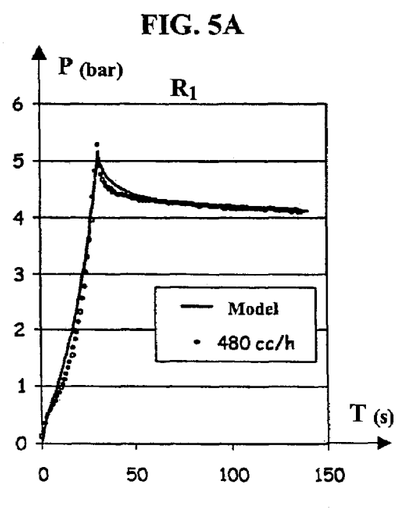
FIGS. 5A to 5D show, for the previous four rocks, the accuracy obtained in the adjustment of the modelled pressure curves in relation to the experimental curves in cases where a first procedure described hereunder is used.
Figure 5B:
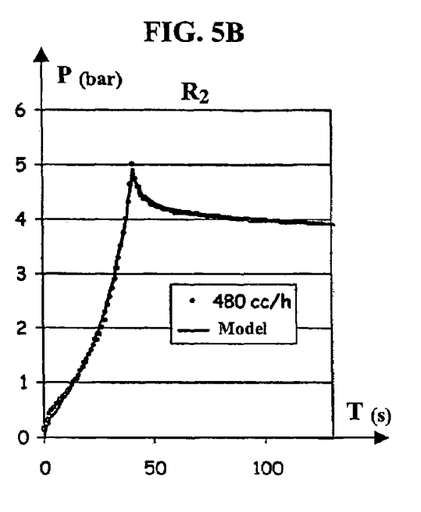
Figure 5C:
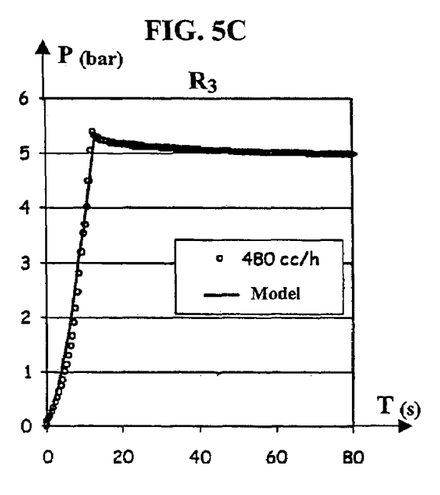
Figure 5D:
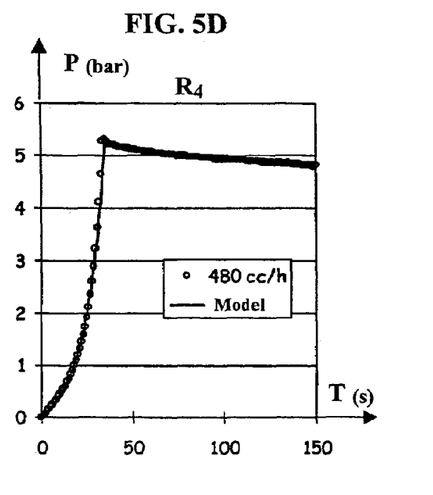
Figure 10:
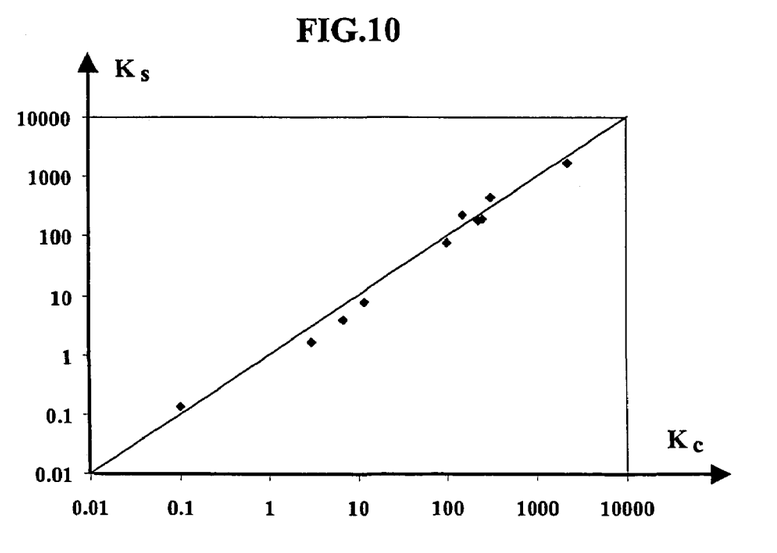
FIG. 10 shows the good match between the permeabilities obtained according to the third procedure, with measurements performed on cores.

In all these cases, a very good match is observed between the simulations and the experimental results. The results obtained by applying the method are quite comparable to those obtained in the laboratory after long conditioning periods using conventional methods for several rocks of different permeabilities, as shown by FIG. 4 (procedure 1) and FIG. 10 (procedure 3).

Programming this modelling within a code allows to calibrate the experiments by means of an optimization loop, which allows the corresponding value of K to be rapidly deduced.

The invention claimed is:

1. A method for evaluating, with a same equipment, physical parameters including at least absolute permeability and porosity of rock fragments (F) taken in a porous medium, comprising a stage of immersing fragments contained in a containment chamber in a viscous fluid and of communicating the chamber containing the fragments with a source for injecting fluid under pressure so as to compress the gas trapped in the pores of the rock, a stage of measuring a physical quantity indicative of evolution of fluid absorption by the rock, modeling evolution of the physical quantity in the chamber, from initial values for the physical parameters of rock fragments (F), and a stage of iterative adjustment of values of the physical parameters of the rock fragments so as to obtain the best possible adjustment of the modeled evolution with the measured evolution of the physical quantity in the chamber, characterized in that:

during the stage of immersion, in the viscous fluid, of the rock fragments contained in containment chamber, an injection pressure of the fluid or of a volume of fluid injected is measured, during the modeling stage, the evolution of the injection pressure of the fluid or of the volume of fluid injected is modeled from initial values selected a priori for absolute permeability (K) and the residual gas saturation and porosity ($\Phi$), and during the adjustment stage, the value of the absolute permeability and of the porosity of the rock fragments is iteratively adjusted so as to obtain the best possible adjustment between the modelled pressure or injected volume evolution and the measured evolution of the pressure or of the volume injected in the chamber.

2. A method as claimed in claim 1, characterized in that the stage of communicating the vessel containing a fluid at a predetermined pressure with a viscous fluid comprises a short communication time so as to cause a fast pressure increase in the chamber and compression of the gas trapped in the pores of the rock, followed by a relaxation period after isolation of the chamber, and the evolution of the pressure in the chamber during the two periods is measured.

3. A method as claimed in claim 1, characterized in that the stage of communicating the chamber with a viscous fluid comprises communicating the chamber with the vessel containing fluid at a predetermined pressure so as to cause a fast and prolonged pressure increase in the chamber and compression of the gas trapped in the pores of the rock, and the evolution of the volume of fluid injected as a function of time is measured.

4. A method as claimed in claim 1, characterized in that the containment chamber is filled with drilling cuttings.

5. A method as claimed in claim 4, characterized in that the containment chamber is filled with previously cleaned rock fragments.

6. A method as claimed in claim 4, characterized in that the containment chamber is filled with rock fragments invaded by drilling fluids.

7. A method as claimed in claim 6, characterized in that said vessel is a surge bottle containing viscous oil and a gas cap at a predetermined pressure.

8. A method as claimed in claim 1, characterized in that the containment chamber is filled with rock fragments obtained by crushing cores taken in a well.

9. A method as claimed in claim 8, characterized in that the containment chamber is filled with rock fragments obtained by crushing cores obtained by sidewall coring of a well.

10. A method for evaluating, with a same equipment, physical parameters including at least absolute permeability and the porosity of rock fragments (F) taken in this porous medium comprising a stage of immersing rock fragments contained in a containment chamber in a viscous fluid and of communicating the chamber containing the rock fragments with a source for injecting fluid under pressure so as to compress the gas trapped in the pores of the rock, a stage of measuring a physical quantity indicative of evolution of the fluid absorption by the rock, modeling evolution of the physical quantity in the chamber, from initial values for the physical parameters of rock fragments (F), and a stage of iterative adjustment of values of the physical parameters of the rock fragments so as to obtain the best possible adjustment of the modeled evolution with the measured evolution of the physical parameter in the chamber, characterized in that:

it comprises a prior stage of feeding the washed and dried rock fragments into containment chamber which is first communicated with a gas tank at a predetermined pressure, so as to determine a solid volume of said rock fragments, an envelope volume and a mass of the fragments are measured, and the porosity and the density of the rock fragments are deduced therefrom, during the stage of immersion, in the viscous fluid, of the rock fragments contained in containment chamber, an injection pressure of the fluid or of the volume of fluid injected is measured, during the modeling stage, the evolution of the injection pressure of the fluid or of the volume of fluid injected is modeled from initial values selected a priori for permeability (K) and a residual gas saturation, and from the value measured for porosity ($\Phi$), and during the adjustment stage, only the absolute permeability value of the rock fragments is iteratively adjusted so as to obtain the best possible adjustment between the modeled pressure or injected volume evolution and the measured evolution of the pressure or of the volume injected in the chamber.

11. A device for evaluating physical parameters of rock fragments (F) taken in a porous medium, comprising a containment chamber for the rock fragments, means for injecting first a viscous fluid into the chamber so as to fill the chamber containing the rock fragments, and for carrying out a cycle comprising a stage of fluid injection into the chamber, means for measuring the evolution of a physical quantity in the chamber and a processing system for modeling the evolution of said physical quantity from initial values selected for the physical parameters of the rock fragments, and for adjusting iteratively the values to be given to these physical parameters so as to obtain the best possible adjustment between the modeled evolution of the physical quantity and the measured evolution of said quantity in the chamber, characterized in that it comprises a vessel containing a fluid at a determined pressure and means controlled by the processing system and intended to control communication of the vessel with the chamber containing the rock fragments.

12. A device as claimed in claim 11, characterized in that it comprises means for measuring the evolution of the pressure in the chamber, as a function of time, the processing system being suited for modeling the evolution of the pressure from initial values selected for the physical parameters of the rock fragments, and for iteratively adjusting values to be given to these physical parameters so as to obtain the best possible adjustment between the modeled pressure evolution and the measured evolution of the pressure in the chamber.

13. A device as claimed in claim 11, characterized in that it comprises means for measuring an evolution of the volume of oil injected in the chamber, as a function of time, the processing system being suited for modelling the evolution of the volume injected from initial values selected for the physical parameters of the rock fragments, and for iteratively adjusting values to be given to these physical parameters so as to obtain the best possible adjustment between the modelled injected volume evolution and the measured evolution of the volume of fluid in the chamber.

14. A device as claimed in claim 13, characterized in that means for measuring the evolution of the volume of fluid injected comprise a flowmeter or differential pressure detector.

15. A device as claimed in claim 11, characterized in that it comprises a gas tank that can be communicated with the chamber by means of a valve, an instrument for measuring an envelope volume so as to determine a porosity of the rock fragments and means for measuring the mass of the rock fragments.

16. A device as claimed in claim 15, characterized in that the means for measuring the envelope volume of the rock fragments to be tested comprise a powder pycnometer.

* * * * *